United States Patent
Jordan et al.

(10) Patent No.: US 9,901,475 B2
(45) Date of Patent: Feb. 27, 2018

(54) FIBER REINFORCED COMPOSITE ORTHOSES

(71) Applicant: Camp Scandinavia AB, Helsingborg (SE)

(72) Inventors: Heinrich Jordan, Ystad (SE); Olof Eklund, Helsingborg (SE)

(73) Assignee: Camp Scandinavia AB, Helsingborg (SE)

( * ) Notice: Subject to any disclaimer, the term of this patent is extended or adjusted under 35 U.S.C. 154(b) by 0 days.

(21) Appl. No.: 15/094,014

(22) Filed: Apr. 8, 2016

(65) Prior Publication Data

US 2016/0220408 A1    Aug. 4, 2016

Related U.S. Application Data

(63) Continuation of application No. PCT/IB2014/002803, filed on Oct. 10, 2014.

(60) Provisional application No. 61/890,296, filed on Oct. 13, 2013.

(51) Int. Cl.
*A61F 5/01*       (2006.01)
*A61F 5/058*      (2006.01)

(52) U.S. Cl.
CPC .......... *A61F 5/0113* (2013.01); *A61F 5/0102* (2013.01); *A61F 5/0111* (2013.01); *A61F 5/0585* (2013.01)

(58) Field of Classification Search
CPC .. A61F 5/00; A61F 5/01; A61F 5/0102; A61F 5/0585; A61F 5/0104; A61F 5/0111; A61F 5/0113; A61F 5/04; A61F 5/05; A61F 5/058; A61F 5/05825; A61F 5/05841

USPC ............................... 602/5, 23, 27, 28
See application file for complete search history.

(56) References Cited

U.S. PATENT DOCUMENTS

| | | |
|---|---|---|
| 3,768,760 A | 10/1973 | Jensen |
| 3,959,544 A | 5/1976 | Rogers |
| 4,089,071 A | 5/1978 | Kalnberz et al. |
| 4,622,254 A | 11/1986 | Nishimura et al. |
| 4,688,338 A | 8/1987 | Brown |
| 5,019,312 A | 5/1991 | Bishop |
| 5,306,557 A | 4/1994 | Madison |
| 5,312,669 A | 5/1994 | Bedard |
| 5,624,386 A | 4/1997 | Tailor et al. |
| 6,146,344 A | 11/2000 | Bader |
| 6,485,661 B1 | 11/2002 | Brown |
| 6,641,893 B1 | 11/2003 | Suresh et al. |

(Continued)

FOREIGN PATENT DOCUMENTS

| | | |
|---|---|---|
| EP | 0934749 A1 | 8/1999 |
| EP | 2524674 A1 | 11/2012 |
| WO | 2008036034 A1 | 3/2008 |

OTHER PUBLICATIONS

International Search Report and Written Opinion for PCT/IB2014/002803, dated Jul. 28, 2015, 15 pages.

*Primary Examiner* — Keri J Nelson
(74) *Attorney, Agent, or Firm* — Grasso PLLC

(57) ABSTRACT

Composite fiber reinforced orthoses are described with respect to fiber orientation of layers making up the laminate and with respect to load to strength ratios, safety zones, loading zones and relationships between these zones. Orthoses involved are such as ankle-foot orthoses, which include the subset of knee ankle-foot orthoses.

19 Claims, 6 Drawing Sheets

(56) References Cited

U.S. PATENT DOCUMENTS

| | | | |
|---|---|---|---|
| 6,887,213 B2 * | 5/2005 | Smits | A61F 5/0111 |
| | | | 602/23 |
| 7,270,644 B2 * | 9/2007 | Ingimundarson | A43B 13/026 |
| | | | 602/16 |
| 7,513,880 B2 | 4/2009 | Ingimundarson et al. | |
| 7,832,117 B2 | 11/2010 | Auger et al. | |
| 8,480,604 B2 * | 7/2013 | Messer | A61F 5/0111 |
| | | | 602/27 |
| 2006/0222837 A1 | 10/2006 | Kismarton | |
| 2012/0295057 A1 | 11/2012 | Atorrasagasti | |

\* cited by examiner

FIBER REINFORCED COMPOSITE ORTHOSES

RELATED CASES

This application is a continuation of PCT international application PCT/IB2014/002803, which was filed on Oct. 10, 2014. The '803 application claims priority to U.S. provisional application No. 61/890,296, which was filed on Oct. 13, 2013 and is entitled Fiber Reinforced Composite Orthoses. The entirety of the '296 provisional application and the '803 international application are incorporated by reference into this application.

TECHNICAL FIELD

Fiber reinforced composite orthoses having multiple fiber reinforced layers are provided. More specifically, processes, systems, devices, and articles of manufacture are provided involving composite laminar orthoses with fiber reinforcement where the relative orientations of the reinforcing fiber vary in relation to a shared reference axis.

BACKGROUND

Orthoses are often considered to be devices, external of the body, that serve to or are used to alter, modify or support structural and/or functional characteristics of the body's skeletal or neuromuscular systems. For example, an orthosis may be used to retard the progression of scoliosis or may be used to assist a person, such as a person suffering with foot nerve damage, with walking. Orthoses can provide confinement and support in static situations, such as in retarding further spinal curving of a patient with scoliosis, and in dynamic situations, such as with supporting and influencing gait of a patient suffering from drop foot. An orthosis may also immobilize, limit, steer, guide or dictate the position or range of motion of a body extremity, a body joint, or a body area. Orthoses may be used for treatment, improved lifestyle, improved comfort, and for other reasons as well.

In certain orthoses, the weight of the wearer's body may be transferred through the orthosis, and certain orthoses may be used for restorative effects during rehabilitation. Ankle Foot Orthoses ("AFOs") and the more specific Knee Ankle Foot Orthoses ("KAFOs"), are examples of orthoses whose names identify the body parts that they are designed to supplement, restrict, guide, support or otherwise assist.

An orthotist may classify an orthosis as being a static orthosis or a functional orthosis. For example, a static orthosis may be used to stabilize a joint and surrounding soft tissue after surgery, hence it is used as an immobilization device. A functional orthosis, on the other hand, can be used to guide a joint to regain or maintain the normal joint function and/or to support a joint and/or surrounding soft tissue to ameliorate neuromuscular weakness. Orthoses used to guide or support a user through an activity or movement such as normal gait, can be equipped with external joints, often called articulated orthoses, such as articulated Ankle Foot Orthoses.

BRIEF DESCRIPTION

Composite orthosis performance may rely on many factors including material properties, manufacturing techniques, and component shape, sizing, and positioning. Composite material properties may depend on: the type of resin or polymer matrix being used and the type, size, location, and orientation of internal fiber reinforcement. Manufacturing techniques that influence performance may include curing temperature and curing pressure.

Composite materials from which orthoses may be manufactured may include layers of polymer or resin, reinforced with fiber. These composite layers may have fiber generally oriented in a single direction, i.e., be considered unidirectional ("UD"), and may have fibers oriented in two-directions, i.e., be considered bidirectional ("BD"). Bidirectional layers may be constructed by weaving the fibers in patterns such as plain, twill, satin or with other variations. These woven fiber arrangements may also be referred to as a two-dimensional layer.

A single shared orthogonal reference axis may be used when describing reinforcing fiber orientation in a single layer, as well as when describing reinforcing fiber orientation when multiple layers are used in a laminate composite. For example, a UD layer may be described as UD 45°, meaning the layer has reinforcing fiber running in the same orientation along a line laying at angle 45° to the right of the y-axis of a reference axis. Similarly, a layer described as UD −45° has reinforcing fiber running in an orientation along a line laying at angle 45° to the left of the y-axis of the same reference axis.

Bidirectional layers may also be referenced with the use of a reference axis. For example, when the orthogonally oriented fibers of a BD woven layer are aligned with the x-axis and y-axis of a reference axis, the layer may be referred to as a 0°/90° weave. And, should this weave be rotated 30° counter-clockwise it may then be identified as a 30°/60° weave to reflect that the fibers in the woven layer are oriented 30° and 60° in relation to the y-axis of the reference axis.

Thus, when fiber reinforced layers are stacked, the resulting stack may be summarized by indicating the relative orientation of the fibers in each layer from a shared reference axis. For example, a stack labeled as 30°, 60°, 45°, 0°/90°, 30°/60°, and 0°/90° indicates some woven layers with fiber orientations the same as the reference axes (x and y axes); and some woven layers with fiber orientations rotated 30° and 60° off of the reference axis; and UD layers with fiber orientations of 30°, 45°, and 60° from the reference axis (in-review: UD 30°, UD 60°, UD 45°, woven 0°/90°, woven 30°/60°, and woven 0°/90°).

The fiber orientation of the various layers in a stack can serve to change the mechanical properties of the stack, including the strength, flex, strain, and toughness of the stack. In other words, a multi-layer stack of woven fiber reinforced layers having a relative fiber orientation of 0°/90°, 30°/60°, and 0°/90° has different mechanical properties than a multi-layer stack of the same material with a relative fiber orientation of 30°/60°, ±45°, 30°/60° or even a stack of 0°/90°, 30°/60° and 30°/60°.

In embodiments, BD and UD layers may be layed up in a stack during manufacture such that their internal fibers are oriented along axes of orientation that differ relative to the fiber orientations of other layers of the stack. In so doing, because several orientations are used, external loading, which may occur in numerous directions during an activity, may be more likely to be oriented along or near an axis of fiber reinforcement of one or more layers. Thus, a laminate orthosis may be layed up such that the reinforcing fibers of BD layers, or UD layers, or both are oriented in differing specific directions relative to a shared reference axis. Fiber orientations in the stack relative to a reference axis may be used to obtain desired stiffness or strain outcomes in targeted areas of the orthosis to potentially alter the performance and functionality of the targeted area of the orthosis and/or to potentially alter the performance and functionality of an orthosis. Similarly, in embodiments, the fiber orientations in a stack relative to a reference axis may also be used to maintain or promote expected load to maximum composite laminated strength ratios ("load to maximum strength ratio"), which is a ratio setting the expected load on an area in relation to the maximum stress the same area of a composite can withstand prior to damage initiation, in safety zones and loading zones designated throughout the orthosis.

The targeted areas may be positioned at various regions of the orthosis for enhanced or altered performance. In embodiments such as an AFO, which includes the KAFO subset, the targeted safety and loading zones may be above and below the ankle of a wearer and may be along a supporting area, such as a strut that connects a lower leg support of the orthosis to the footplate of the orthosis. Through selective orientation of fibers in reference to an axis, predicted stresses from external loads can be compared to maximum composite laminate strength for the same area (i.e., load to maximum strength ratio) to consider whether laminate composite strength is adequate and whether laminate composite strength in a first area is suitable as compared to a second area of an orthosis. Suitability may be determined by whether damage initiation of the composite laminate is expected, whether damage initiation of the composite laminate is not expected, and whether the ratio of load to maximum strength is sufficiently larger or smaller than another area upon which load to maximum composite laminate strength will be determined. The global loading of an orthosis, e.g., torsional, tensile, and compressive loads, cause stresses in the material that may be managed. These stresses, acting on the lamina level, being managed may include interlaminar and in-plane shear stresses, as well as compressive and tensile stresses. Predicting critical internal material stress during normal usage and maximum composite laminate strength failure may employ tools such as Tsai-Wu and Tsai-Hill or other failure analysis criteria suitable for composite laminates.

In embodiments, a ratio may be considered comparing areas of a strut of an orthosis spanning an ankle where the load to maximum strength ratio of a safety zone above the ankle is smaller than a ratio of the load to maximum strength ratio of a loading zone below the ankle. Thus, during normal use and loading, the first area of the orthosis, e.g., an upper area of a strut of an AFO, may be less flexible and have a smaller load to maximum strength ratio than a second area of the orthosis, e.g., a lower area of the strut of an AFO.

In embodiments, relative fiber orientation between layers considering a common reference axis or reference line, may be specified such that orthosis may be designed to provide low load to maximum strength ratio areas ("safety zones") and high load to maximum strength ratio areas ("loading zones"). These zones may be provided so that areas with high load to maximum strength ratios may be located around the footplate or in the lower strut, and areas with lower load to maximum strength ratios may be located in the upper part of the strut and perhaps into the lower leg support as well. The location of these safety and loading zones and their position relative to each other may be used to affect orthosis performance.

Adjustment to load to maximum strength ratios for an area of the orthosis may be achieved by varying the fiber orientation of a layer and the orientation of surrounding layers as well. Other adjustments to the composite laminate, such as varying the shape of a layer or layers, may also be employed.

In embodiments, when the load to maximum strength ratio above the ankle is smaller than the same ratio when considered for areas below the ankle or at the ankle, suitable flexibility and strength may be introduced into the design and into certain locations of the design. In embodiments, the suitable flexibility and strength may be prescribed into AFOs to accommodate the higher relative flexure of the foot below the ankle than the fairly low flexure typically experienced above the ankle when walking. In other words, the ratio of expected load to maximum composite material strength for different areas of an orthosis may be prescribed to provide for more flexure in the orthosis below the ankle than above the ankle in order to accommodate the human anatomy, which itself provides for more flex in the bones, muscles, and ligaments of the foot and ankle than the bones, muscles, and ligaments of the lower leg above the foot.

The tolerable peak loads of the target areas, in other words the quantity of stress that does not exceed the maximum laminate strength, may be prescribed by selective orientation of layers constituting the target areas. In embodiments this may include laying up three or more, BD layers adjacent to one another without intervening UD layers. It may also include using all fiber reinforcement, all glass reinforcement, other reinforcement fibers, and combinations of these or other reinforcement fibers in layers.

Still further, embodiments may also include orienting fiber reinforcement of layers in prescribed different or the same orientations relative to a geometrical reference axis of the orthosis. In other words, fibers of several layers of a stack may be orientated to follow, cross, or intersect at a certain angle from a shared orientation. Selective orientations may also include setting fiber orientations for weaved layers making up an orthosis, where the two angles of the reinforcing fiber of a BD layer do not have one axis laying along 0°, 30°, 45°, 60° and 90° relative to a shared reference orientation axis.

In embodiments, the various prescribed fiber orientations of the layers may be obtained by cutting uniformly shaped pieces at different orientations from the same prepreg. In other words, if an identically shaped BD layer needs to be manufactured with two different orientation axis, the same stencil may be used to cut the shape from the prepreg and the stencil may be rotated such that the weave pattern of the BD fiber is oriented in different directions for some or all of the shapes being cut with the stencil form the prepreg. Through the change in orientation of the stencil relative to the fiber of the prepreg, the fiber orientations of the cut out shapes may vary by a few degrees or by several and can include relative angles such as the following: 0°/90°, 30°/60°, ±45°, 10°/80°, 12°/78°, 20°/70°, and 35°/55°. Other orientations may be used, including ones that differ by five degrees more or by five degrees less than the preceding list of angles. By using these or other non-conventional orientation angles non-uniform or unequal performance may be created and may be used to desired support during walking or other support functions of an orthosis.

Here, as elsewhere, dry fiber techniques may also be used instead of or in combination with prepreg technologies. Also, during manufacture, fiber orientation may be adjusted as prepreg or dry fiber techniques are employed and layers are stacked and aligned in lasts or forms serving to shape the layers into their final three-dimensional shape. Thus, in embodiments, fiber may be oriented a certain way at the beginning of manufacture but may be slightly reoriented during manufacture as the layers are worked and aligned into molds or onto lasts. These adjusted fiber orientations may be set into their new orientation during the curing process.

BRIEF DESCRIPTION OF THE SEVERAL
VIEWS OF THE DRAWINGS

DETAILED DESCRIPTION

Figure 1:
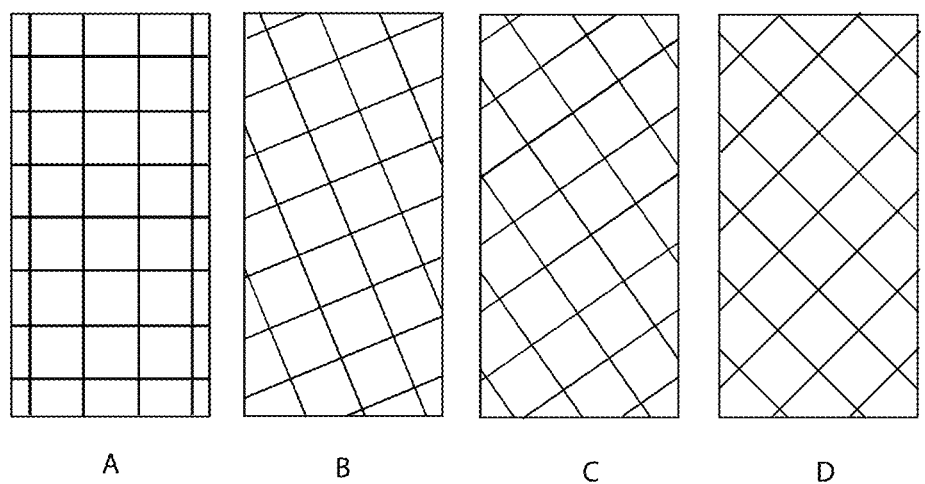
FIG. 1 shows weaved layers having the same shape but different fiber orientations as may be employed in embodiments.

Various methods, uses, devices, systems, and articles of manufacture may be provided. These include laminate composite orthoses with BD fiber orientations where at least some layers have fiber orientations relative to a shared conventional orientation axis different than 0°, 30°, 45°, 60°, and 90°. Embodiments may also include AFOs, which includes the subset of KAFOs, where load to maximum strength ratios are employed to manage and set fiber orientation in layers of a composite constituting an orthosis such that safety zones and loading zones of various magnitudes and relative magnitudes may be employed in various zones of the orthosis.

In embodiments, fiber orientation may be modified to provide for variations in load to maximum strength ratios throughout an orthosis. These variations may be introduced to develop suitable load to maximum strength ratios in various areas of an orthosis and between various areas of an orthosis. For example, it may be suitable to have a strut of an AFO where the expected load to maximum strength ratio at an upper part of the strut is smaller than the same ratio when considering an area in the lower part of the strut. Thus, in a strut traversing the ankle of a wearer, comparisons may be made between the peak expected loading stress and the maximum material strength for a target zone above the ankle, about the ankle, and below the ankle. The expected loading may be set from expected deflections associated with normal gait. In so doing, acceptable strength may be maintained above and below the ankle and the strut may be considered to be fine-tuned to be able to mimic the flexure and other movement of the foot, ankle, and lower leg while walking.

Embodiments may include dynamic AFOs made of fiber reinforced composites. These fiber reinforced composite AFOs can be manufactured through a number of methods. For example, dry fiber layup techniques as well as prepreg layup can be used. Fibers suitable for AFO may include carbon, glass, and aramid fibers. Regardless of dry fiber techniques or prepreg layup, different types of fiber orientation can be used. The matrix and additives used to construct the orthosis in embodiments may also vary, for instance, both thermo-set resins such as epoxy and thermoplastic resins such as polyamide, may be used. Additives can come in numerous forms, an example being colorant.

In embodiments having fiber reinforced composites, the load may be carried in the direction of the fiber. In embodiments, brace design of AFO embodiments may be considered in three-dimensions in order to adapt to the organic shape of the lower leg and foot. The fiber orientation may also preferably align with the load applied to the lower leg and foot. In the case of an AFO, the brace may be designed in embodiments to mimic or trace the ankle joint as well as hind-foot, mid-foot, and fore-foot joints.

In embodiments, an AFO, such as a KAFO, may extend both above and below the ankle. In the lower leg, below the knee, most motion takes place at the ankle joint itself or below the ankle. As to anatomy, as the upper part of an AFO can guide the Tibia and Fibula, whereas the lower part is regularly more dynamic to meet the movements normally taking place within the ankle and foot, embodiments may promote support to lower leg and the ankle of a wearer. In calculating load and its ratio to maximum composite laminate strength, the complex load case of an AFO may be considered as movements in three different planes: sagittal, frontal (coronal), and transverse plane. In the sagittal plane, movements such as flexion and extension take place, for example plantar flexion and dorsiflexion of the ankle joint. In the frontal plane, movements such as lateral or medial tilting take place, for example eversion and inversion. In the transverse plane, rotational movements take place. Also, the three planes of movements could be transferred into a coordinate system. For example, in embodiments, the sagittal plane could be the x-axis, the frontal plane could be the y-axis and the transverse plane the z-axis. Each of these movements may be considered when choosing orientation of fibers and other adjustments provided in embodiments herein.

In embodiments, one or more composite layers used in constructing an orthosis may share similar or identical aspects to some or all layers. These aspects may include being partially or fully symmetrical to some or all layers in certain aspects and being unique to some or all layers in certain aspects. The layers may be formed and assembled such that the ratio between the maximum composite laminate strength for an area of the orthosis is larger than one for loads expected for the coinciding area being evaluated. Through controlling maximum composite laminate strength (up or down) for various areas of an orthosis, especially when compared to the same ratio for other areas of the orthosis, safety zones and loading zones, may be created in the orthosis. Furthermore, the orthosis may function in embodiments such that it is better adapted for the relative movement above the ankle of a wearer and is better adapted for the relative movement at or below the ankle of a wearer.

Safety zones in the orthosis may be created in embodiments through layer configuration, composition, orientation, and placement and through fiber orientation. In embodiments, a ratio between expected loads to maximum composite laminate strength ("load to maximum strength ratio")

may be considered for various areas of an orthosis. This ratio is preferably lower than one for a particular area because a value of one or more signifies composite damage initiation. Areas with lower load to strength ratios may be considered safety zones while areas with load to strength ratios closer to one may be considered loading zones. The ratio between safety zones and loading zones, or other areas, may also be considered to evaluate and tailor expected orthosis performance. In addition, selective placement of safety zones, loading zones, and their combination, may be used to manage orthosis performance.

In embodiments, safety zones, for example, may be located at upper portions of an AFO or other orthosis strut, where the strut serves to connect with a lower leg connector. Likewise, loading zones, may themselves be located in embodiments, for example, at lower portions of an AFO or other orthosis strut connecting to a footplate. The position and difference in the magnitude between the load to strength ratio of the safety zone and the load to strength ratio of the loading zone can serve to both predict and tailor the performance of the orthosis as well as the ability to manage composite damage initiation.

In embodiments, layers may be configured such that load to strength ratios are managed to be lower in safety zones and higher in loading zones. Still further, in embodiments, comparative ratios between load to strength ratios in loading zones located in the lower end of the strut when compared with safety zones located at the upper end of a strut in the same orthosis may preferably be above 1.0 in embodiments. This loading zone to safety zone quotient can serve to reflect and tailor expected orthosis performance.

A revised load to strength ratio may have a corresponding effect whereby other areas of the orthosis are subject to more stresses during expected loading. This combination of the revised load to strength ratio and the transfer of stresses elsewhere in the orthosis can serve to promote safety zones, loading zones, and affect orthotic performance.

In embodiments described herein and others not described, supporting struts, strut footplate interfaces, opposing thirds of a strut or footplate, and other areas of an orthosis, can each comprise layers as discussed herein and may each employ the load to strength ratio in various areas.

Thus, in embodiments, orthosis may be designed such that the ratio of expected stresses from loads, as related to the maximum composite tolerable laminate strength of target areas, may be decreased in certain areas of the orthosis where lower stresses are preferred and may be increased in other areas of the orthosis where higher material stresses are acceptable.

As related to loading that may occur and for accommodations of designs and teachings provided herein, during normal gait the ankle motion during a stride may involve a range of plantar flexion up to 20° or so and dorsiflexion up to 10° or so. In the subtalar joint, normal gait may involve a range of inversion (medial tilt) up to 10° or so and eversion (lateral tilt) up to 10° or so. These degrees may change substantially if the activity "gait" is changed to the activity "descend stair", for example. In the latter activity, the movement dorsiflexion may reach a value of 35° or so. If the activity performed is "ascend stair" the plantar flexion may reach 40° or so. Range of movement along different planes or axis may also be affected by deficiencies such as neuromuscular weaknesses or diseases, neurological disorders or birth defects among others. Depending on how the deficiencies present, the impaired gait may involve limitation to the range of movement as well as expended range of movement. Both normal and impaired gait are also affected by movements from the complexity of joints above the ankle, knees and hip belonging to the lower extremities, as well as pelvis and trunk. As a step progresses the whole body propels forward and movements take place in all three planes. A composite AFO can serve to address movements in all three planes and fiber layup should preferably be tailored to meet load situations as well as anatomical shapes.

FIG. 1 shows four BD single layer weaves. Composite A is the shape of a rectangle and has a weave with relative fiber angles of 0°/90°; composite B shares the same rectangular shape and has a weave with relative fiber angles of 78°/12°. Composites C and D also share the rectangular shape with composite C having a relative fiber angle of 60°/30° and composite D having a relative fiber angle of ±45°.

Figure 2:
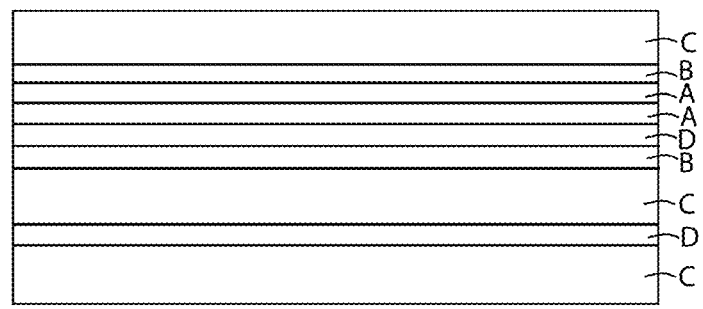
FIG. 2 shows a stack of layers, using the four weaved layer orientations of FIG. 1, as may be employed in accord with embodiments.

FIG. 2 shows how composite BD weaves A-D may be stacked atop one another in some embodiments. FIG. 2 shows how in some embodiments the layers may be directly adjacent without intervening UD layers, however, intervening UD layers may also be employed in embodiments. FIG. 2 also shows that layer C is thicker than the other three layers. The reinforcing fibers in these layers as well as in embodiments may be carbon, glass, aramid, and other materials as well. FIG. 2 also shows that there may be the same layer stacked upon itself in certain embodiments and that there may or may not be symmetry about a central or core layer with respect to a pattern of additional layers placed above and below the central or core layer.

In certain embodiments, three or more woven layers may be stacked atop one another, where each layer shares the same or a similar geometric form and the orientation of the woven fibers with respect to a shared orientation reference contains two orientations at least along a 0°, 30°, 45°, 60° or 90° axis orientation and one layer having an orientation different than 0°, 30°, 45°, 60°, and 90° and perhaps not evenly divisible by 15° as well. This stack of three or more layers may further contain other layers, and one or more additional layers weaved or UD with a fiber orientation different than 0°, 30°, 45°, 60°, and 90° when considering the same shared reference axis of the three group stack.

In embodiments, the layers may be constructed using prepreg as well as dry fiber layup techniques. Other assembly variations or techniques and various other manufacturing techniques may also be used.

Figure 3:
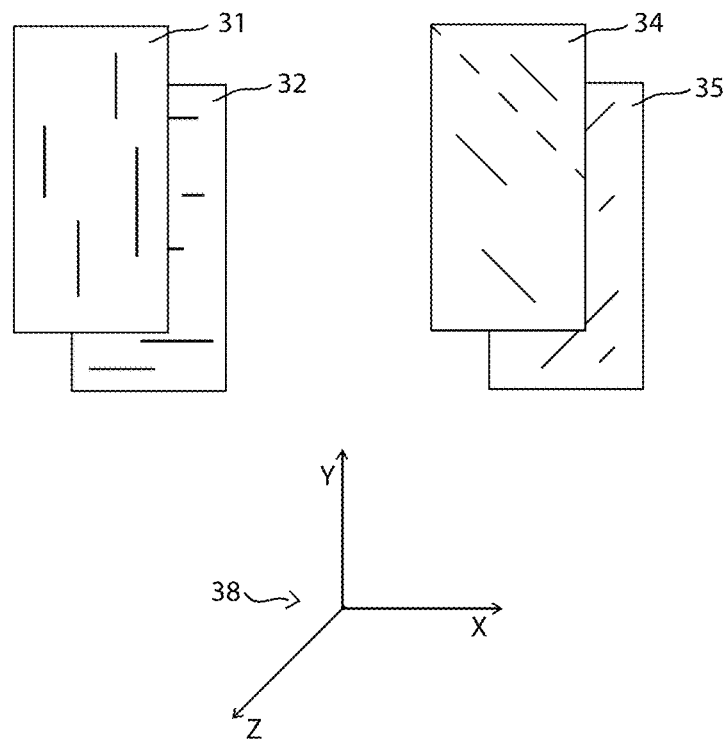
FIG. 3 shows UD fiber reinforced layers, their reinforcing fiber orientation, and a shared reference axis as may be employed in accord with embodiments.

FIG. 3 shows orientation axes 38 and four UD fiber reinforced layers 31, 32, 34, and 35 as may be employed in embodiments. As can be seen, the fiber orientation in layer 31 is vertical and the fiber orientation in layer 32 is horizontal. As can be further seen, unidirectional layers 34 and 35 have fiber orientations set at ±45° relative to the y-axis of the reference axes 38. In embodiments, UD layers may be used with BD layers to provide safety zones and loading zones in targeted areas of an orthosis. These targeted areas may be above and below the ankle in an orthosis and, furthermore, the relative ratio of the safety zones to the loading zones may have a quotient of 1.0 or greater when comparing loading zones in a target area below the ankle in the orthosis with safety zones in a target area above the ankle. The load to maximum strength ratio may be determined using the expected loading in an area compared to the maximum composite laminate strength of that area when damage initiation is reached or is expected to be reached.

Figure 4:
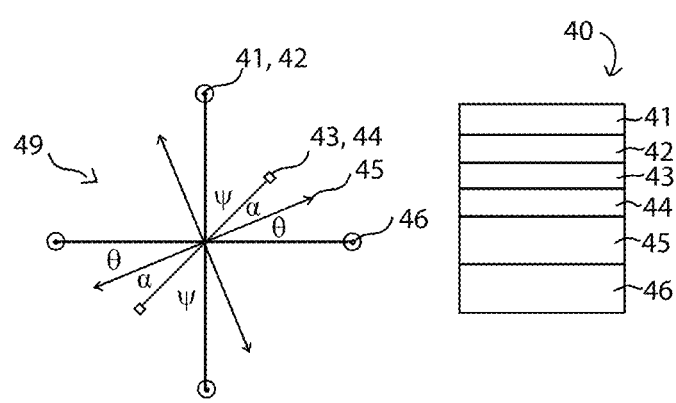
FIG. 4 shows a stack of fiber reinforced layers and the orientation of fibers in the stack relative to a shared reference axis as may be employed in embodiments.

FIG. 4 shows how layers may be stacked in embodiments, such as stack 40. Layers may be UD layers (nos. 41-44) and BD layers such as weaves (nos. 45-46). Layers 41 and 42 may each have 0° fiber orientations relative to y-axis of the reference axes 49 while layers 43 and 44 may have an orientation of 33° (Ψ) relative to the y-axis of the reference axes 49 and layer 45 may have an orientation of 57° (Ψ+α) relative to the same y reference axis. In reference axes 49 symbols Ψ+α+θ equal 90°.

Figure 5:
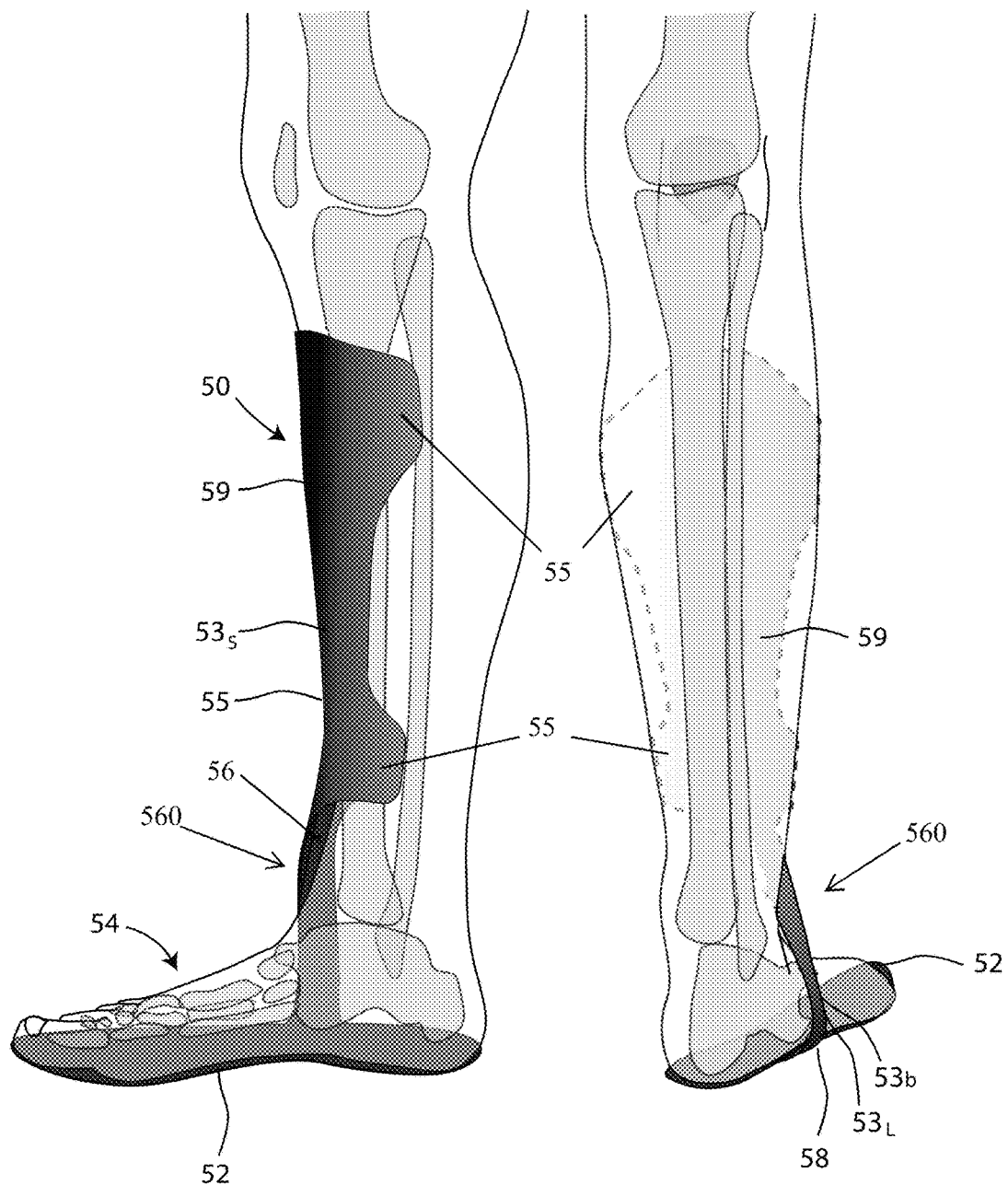
FIG. 5 shows a medial side view and a rear perspective view of an ankle foot orthosis, as may be employed in embodiments, mounted on a lower leg of a user as may be employed in embodiments.

FIG. 5 shows perspective views of a composite laminate AFO 50, as may be employed in embodiments, mounted on the lower leg of a user, as seen from the medial side of the lower leg of the user, and as seen from the posterior side of the lower leg of the user. The composite laminate AFO 50 includes a lower leg support 59, a strut 560, a footplate 52, and four alignment ears 55. While only a single strut is shown in FIG. 5, AFO embodiments may also employ two struts, either on the same side of the leg or on opposite sides of the leg of the user. FIG. 5 also shows how the lower leg, ankle, and foot 54 of a user may be oriented in the orthotic and supported by the orthotic. As can also be seen, the ankle of the user is positioned below the lower leg support 59 and near the strut 560 of the AFO 50. As can also be seen, the footplate 52 of the AFO 50 may be somewhat flat and may reside under most or all of the sole of the foot 54 of a user. In KAFO embodiments, the lower leg support may extend further up the lower leg of the user and may be secured around portions of the knee joint of a wearer.

Safety zones and loading zones may be created or included in accordance with embodiments. A loading zone $53_L$ is shown in FIG. 5, as are safety zones 56 and $53_S$. The safety and loading zones may be located elsewhere as well in embodiments. Moreover, they may be closer together in the strut such that they each reside in the middle third of the length of the strut and/or the top third and bottom third respectively. They may be positioned relative to the orthosis such that they each reside in the middle third of the length of the orthosis and/or the top third and bottom third respectively.

Figure 6:
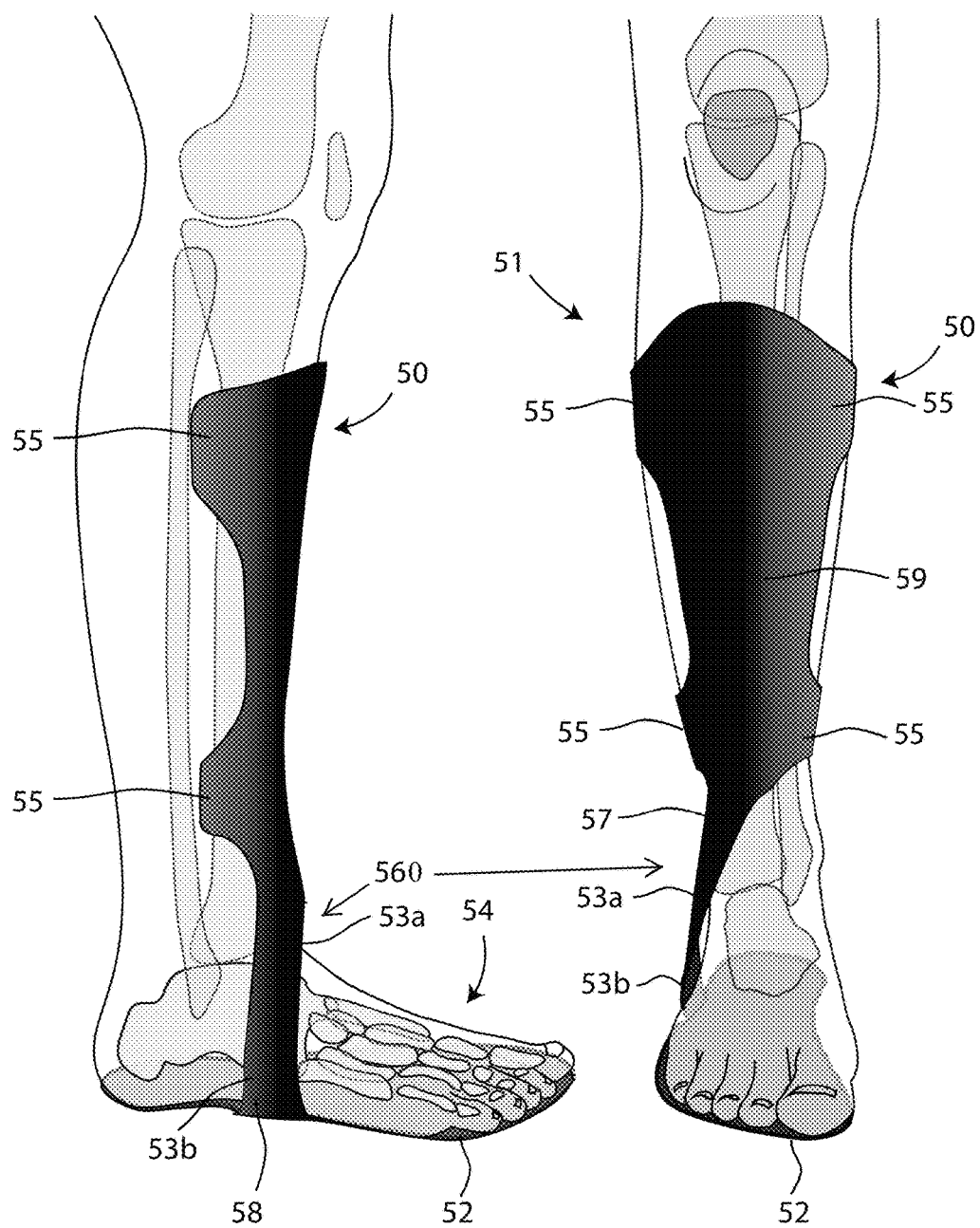
FIG. 6 shows a lateral side view and a front perspective view of an ankle foot orthosis, as may be employed in embodiments, mounted on a lower leg of a user as may be employed in embodiments.

FIG. 6 also shows perspective views of the same composite laminate AFO 50, as may be employed in embodiments, mounted on the lower leg of a user, as in FIG. 5. In FIG. 6, however, lateral and anterior views are shown. The views of FIG. 6 show how a lower leg support 59, strut 560, footplate 52, and four alignment ears 55 may conform with the lateral and anterior side of the lower leg and foot 54 of a wearer.

FIGS. 5 and 6 show safety zones and loading zones as may be created or included in accordance with embodiments. These safety zones are shown at 53a in FIG. 6 and at 53s and 56 in FIG. 5, while the loading zones are shown at 53b of FIGS. 5 and 6 and $53_L$ of FIG. 5. The safety and loading zones may be located elsewhere as well, in embodiments. Also labeled in either FIG. 5 or 6 are lower leg 51, lower leg support 59, upper strut 57, and lower strut 58.

Figure 7:
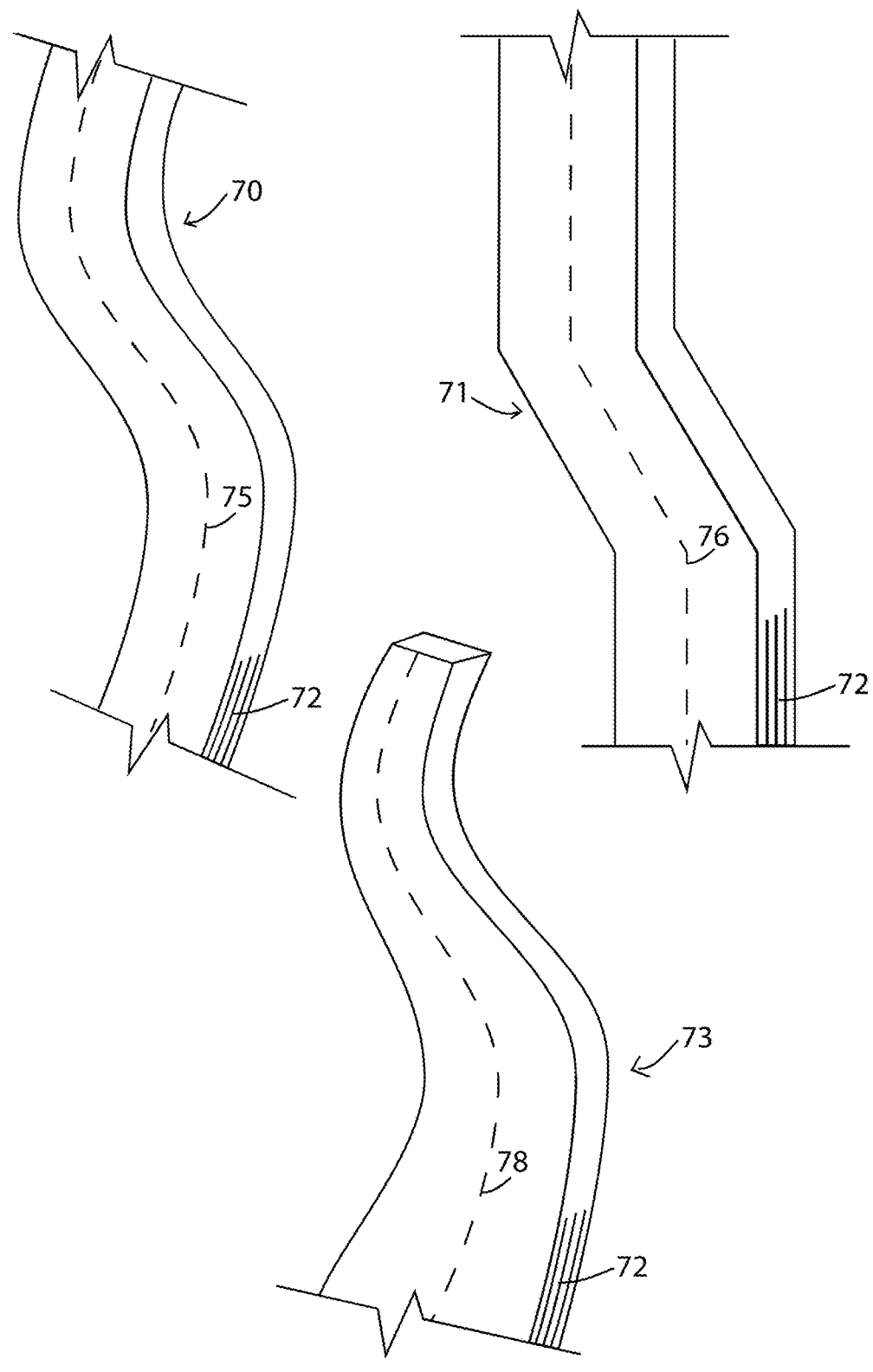
FIG. 7 shows fiber reinforced layers of exemplary components of a composite orthosis, and each of their geometric center-lines, as may be employed in embodiments.

FIG. 7 shows exemplary struts 70, 71, and 73, as may be assembled in accord with embodiments. In embodiments, such struts may be employed in an orthosis and may comprise multiple layers of fiber reinforced composites. Evident in FIG. 7 are the center lines 75, 76, and 78 of the struts shown in the Figure. As can be seen, these center lines may be centered geometrically along the length of the struts and coincide with the turns and bends of the struts. In embodiments, one or more layers may have fibers oriented to follow these center lines or may have a constant angular orientation with relation to the center lines along the length of the strut. Such struts may also comprise layers and other techniques as described herein, and which are labeled at 72.

Figure 8:
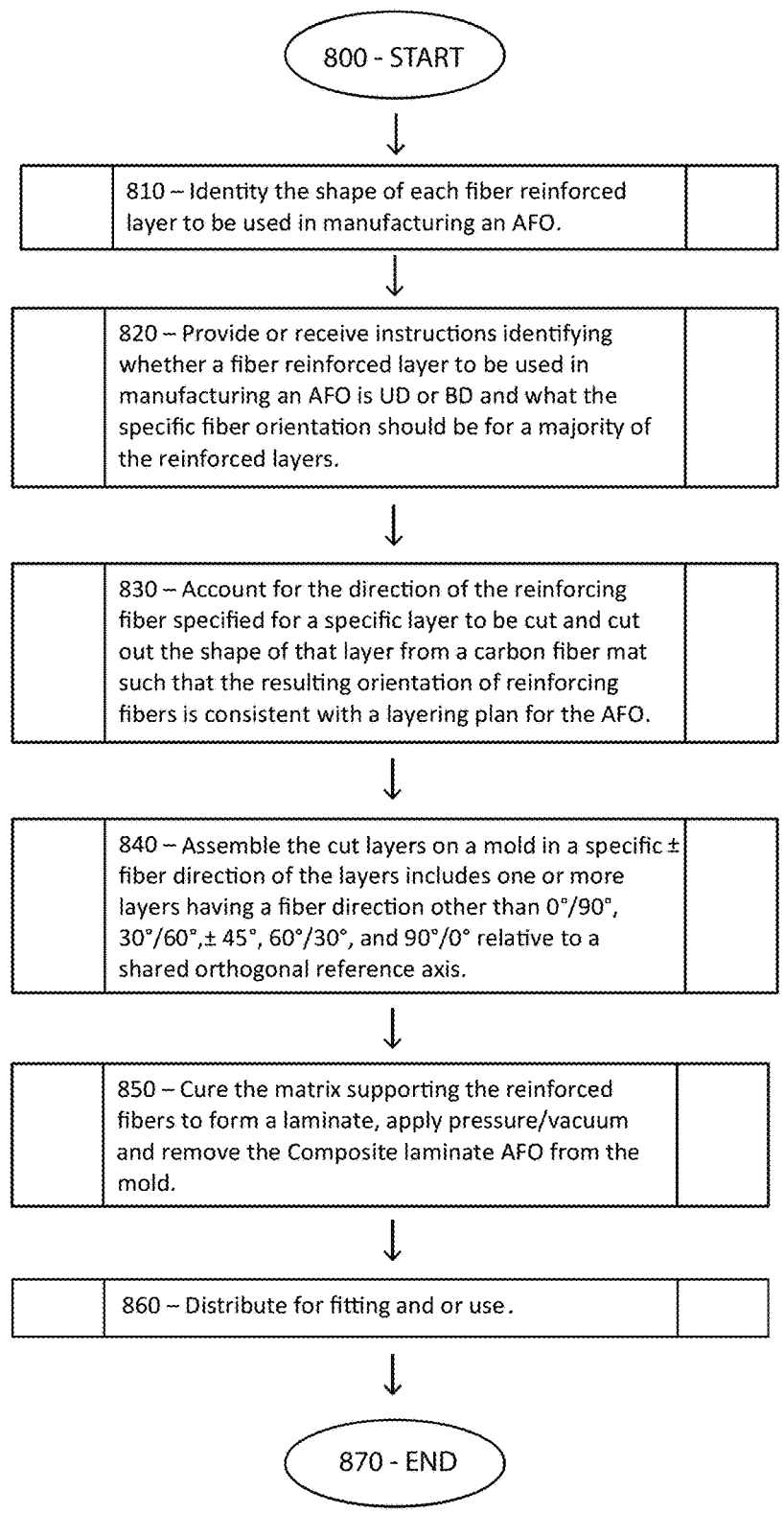
FIG. 8 shows a method of manufacturing an orthosis as may be employed in accord with embodiments.

FIG. 8 shows a method of manufacturing an orthosis such as an AFO (which includes the subset of KAFOs) in accord with embodiments. As shown at 810, a manufacturer may identity the shape of each fiber reinforced layer to be used in manufacturing an AFO. As shown at 820, instructions may be provided or received to identify whether a fiber reinforced layer to be used in manufacturing an AFO is UD or BD and what the specific fiber orientation should be for a majority of the reinforced layers. At 830, an accounting for the direction of the reinforcing fiber specified for a specific layer to be cut may be done, and a cut out of the shape of that layer from a carbon fiber mat may be completed, such that the resulting orientation of reinforcing fibers in that shape is consistent with a layering plan for the AFO being manufactured. At 840, cut layers may be assembled on a last in a specific ± fiber direction of the layers includes one or more layers having a fiber direction other than 0/90, 30/60, ±45, 60/30, and 90/0 relative to a shared orthogonal reference axis. And, at 850, the matrix supporting the reinforced fibers may be cured to form a laminate. Pressure or a vacuum may also be applied, and the composite laminate AFO may be removed from the mold. These products may subsequently be distributed for use as is shown at 860.

Although the foregoing description is directed to the preferred embodiments of the invention, it is noted that other variations and modifications will be apparent to those skilled in the art provided with the disclosure herein, and may be made without departing from the spirit or scope of the invention. For example, as noted above, various types of AFOs, including KAFOs, may employ embodiments. Moreover, features described in connection with one embodiment of the invention may be used in conjunction with other embodiments, even if not explicitly stated in the foregoing. The described embodiments are to be considered in all respects only as illustrative and not restrictive.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specific the presence of stated features, integers, steps, operations, elements, and/or components, but do not preclude the presence or addition of one or more other features, integers, steps, operation, elements, components, and/or groups thereof.

The corresponding structures, material, acts, and equivalents of any means or steps plus function elements in the claims below are intended to include any structure, material or act for performing the function in combination with other claimed elements are specifically claimed. The description of the present invention has been presented for purposes of illustration and description, but is not intended to be exhaustive or limited to the invention in the form disclosed. Many modifications and variations will be apparent to those of ordinary skill without departing from the scope and spirit of the invention. The embodiment was chosen and described in order to best explain the principles of the invention and the practical application, and to enable others of ordinary skill in the art to understand the invention for embodiments with various modifications as are suited to the particular use contemplated.

What is claimed is:

1. An orthosis comprising:
    a foot plate; and
    a first strut connected to the footplate,
        wherein at least either the footplate or the first strut contains three or more bidirectional fiber reinforced layers,
        a first bidirectional layer having a first fiber orientation angle for the fiber reinforcement of the first bidirectional layer, a second bidirectional layer having a second fiber orientation angle for the fiber reinforcement of the second bidirectional layer, and a third bidirectional layer having a third fiber orientation angle for the fiber reinforcement of the third bidirectional layer, the fiber orientation angles of the first bidirectional layer, the second bidirectional layer, and the third bidirectional layer being different from each other with regard to the same reference axis and at least one of the fiber orientation angles relative to the reference axis not being evenly divisible by 15°, the first bidirectional layer, the second bidirectional layer, and the third bidirectional layer being part of a cured laminate.

2. The orthosis of claim 1 wherein the first strut is positioned in the orthosis such that when the orthosis is worn by a user the first strut is positioned to be only on one side of an ankle of the user.

3. The orthosis of claim 2 wherein the quotient of load to maximum strength ratio in a lower portion of the first strut to the load to maximum strength ratio in an upper portion of the first strut is 1.0 or above 1.0.

4. The orthosis of claim 1 wherein the first strut is positioned only on the lateral side of the orthosis.

5. The orthosis of claim 1 wherein reinforcing fiber of bidirectional fiber reinforced layers comprises one or more of carbon, glass, and aramid fibers.

6. The orthosis of claim 1 wherein, when the orthosis is worn, the configuration of the orthosis provides that stresses in relation to maximum composite laminate strength in a lower portion of the first strut resulting from loading created by walking, are greater than stresses in relation to maximum composite laminate strength developed in an upper portion of the first strut.

7. The orthosis of claim 1 wherein the first and second bidirectional layers are adjacent to each other.

8. The orthosis of claim 1 wherein the first and second bidirectional layers are adjacent to each other and the second and third bidirectional layers are adjacent to each other and the third bidirectional layer is a top layer or a bottom layer.

9. The orthosis of claim 1 wherein one or more of the first, second, and third bidirectional layers includes thermo-set or thermo-plastic and wherein there are one or more intervening layers between at least two of the first, second, and third bidirectional layers.

10. The orthosis of claim 1 wherein one or more of the first, second, and third bidirectional layers is taken from prepreg and wherein the first bidirectional layer is the top layer, the second bidirectional layer is a middle layer, and the third bidirectional layer is behind the second layer.

11. A composite fiber reinforced ankle-foot orthosis comprising:

a first fiber reinforced bidirectional layer with reinforcement fibers oriented orthogonally in a first orientation relative to a reference axis;

a second fiber reinforced bidirectional layer with reinforcement fibers oriented orthogonally in a second orientation relative to the reference axis; and a third fiber reinforced bidirectional layer with reinforcement fibers oriented orthogonally in a third direction relative to the reference axis;

wherein the first layer, second layer and third layer are stacked upon each other and cured to each other without an intervening unidirectional layer, and wherein the orientation of one of the bidirectional layers is offset to the reference axis by an angle other than 0°/90°, 30°/60° and ±45°.

12. An ankle foot orthosis comprising:

a strut;

a lower leg attachment; and a footplate;

the strut connecting the lower leg attachment to the footplate;

the strut including layers of fiber reinforced composite wherein a first fiber reinforced composite layer has reinforcing fiber oriented along an axis of an orthogonal reference axes, wherein a second fiber reinforced composite layer has reinforcing fiber oriented at an angle evenly divisible by 15° from an axis of the orthogonal reference axes, wherein a third fiber reinforced layer has orthogonally oriented reinforcing fiber, the orthogonal orientation positioned at an angle not evenly divisible by 15° from an axis of the orthogonal reference axes, and wherein the first fiber reinforced composite layer, the second fiber reinforced composite layer, and the third fiber reinforced layer are part of a cured laminate forming the strut.

13. The orthosis of claim 12 wherein at least the first or second layer comprises unidirectional fiber.

14. The orthosis of claim 12 wherein the strut is positioned to be solely on one side of the ankle of a wearer.

15. The orthosis of claim 12 wherein the strut is positioned only on the lateral side of the orthosis.

16. The orthosis of claim 12 wherein reinforcing fiber of fiber reinforced composite comprises one or more of carbon, glass, and aramid fibers.

17. The orthosis of claim 12 wherein one or more fiber reinforced composite comprises thermo-set or thermo-plastic.

18. The orthosis of claim 12 wherein one or more fiber reinforced composite is taken from prepreg.

19. The orthosis of claim 12 wherein, while the orthosis is being used, the portion of the strut first experiencing composite damage initiation by applied forces resulting from a wearer of the orthosis while walking, is located in the strut at or below an ankle of the wearer.

* * * * *